(12) United States Patent
Johnson

(10) Patent No.: US 11,064,915 B2
(45) Date of Patent: Jul. 20, 2021

(54) FUNCTIONAL REACH ASSESSMENT DEVICE AND METHOD

(71) Applicant: Norman L Johnson, Pittsburgh, PA (US)

(72) Inventor: Norman L Johnson, Pittsburgh, PA (US)

(*) Notice: Subject to any disclaimer, the term of this patent is extended or adjusted under 35 U.S.C. 154(b) by 613 days.

(21) Appl. No.: 15/795,987

(22) Filed: Oct. 27, 2017

(65) Prior Publication Data

US 2018/0116563 A1  May 3, 2018

Related U.S. Application Data

(60) Provisional application No. 62/413,516, filed on Oct. 27, 2016.

(51) Int. Cl.
*A61B 5/11* (2006.01)
*A61B 50/26* (2016.01)
*A61B 5/107* (2006.01)

(52) U.S. Cl.
CPC ............ *A61B 5/1124* (2013.01); *A61B 50/26* (2016.02); *A61B 5/1072* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,083,418 A * | 4/1978 | Hutchinson | ............... | G01G 1/36 177/173 |
| 5,029,047 A * | 7/1991 | Kachel | ................. | A63H 33/006 362/253 |
| 6,389,883 B1 * | 5/2002 | Berme | ................. | A61B 5/4023 73/65.01 |
| 8,758,276 B2 | 6/2014 | Clinton-Barnett | | |
| 8,758,277 B2 | 6/2014 | Rathi | | |
| 8,896,526 B1 | 11/2014 | Park | | |
| 9,753,135 B2 | 6/2017 | Bosch | | |
| 2002/0094748 A1 * | 7/2002 | Baik | .................... | A63H 33/006 446/227 |

(Continued)

OTHER PUBLICATIONS

Tantisuwat et al. Multi-directional Reach Test: An Investigation of the Limits of Stability of People Aged between 20-79 Years. J. Phys. Ther. Sci. 26: 877-880, 2014. (Year: 2014).*

*Primary Examiner* — Etsub D Berhanu
(74) *Attorney, Agent, or Firm* — AP Patents; Alexander Pokot

(57) ABSTRACT

A device that enables an assessment or a management of a medical condition in a patient, includes a base member comprising a pair of surface spaced apart from each other to define a thickness of the base member. The base member can be provided as an elongated base member. Markings are disposed on one surface from the pair of surfaces of the elongated base member along a length of the elongated base member. An array of targets is provided with targets being disposed, during use of the device, below a bottom edge of the elongated base member. Coupling members are also provided with each coupling member coupling a respective target from the array of targets to the elongated base member for a reciprocal linear movement along the length of the elongated base member. The device can be affixed to a structure or provided as a mobile device.

21 Claims, 12 Drawing Sheets

(56) References Cited

U.S. PATENT DOCUMENTS

| | | | | |
|---|---|---|---|---|
| 2004/0005839 | A1* | 1/2004 | Oren | A63H 33/006 |
| | | | | 446/227 |
| 2009/0249632 | A1* | 10/2009 | Tyler | G01B 3/20 |
| | | | | 33/494 |
| 2009/0299233 | A1* | 12/2009 | Wang | A61B 5/4023 |
| | | | | 600/595 |
| 2009/0326607 | A1* | 12/2009 | Castel | A61K 31/202 |
| | | | | 607/48 |
| 2010/0323581 | A1* | 12/2010 | Goszewski | A63H 33/006 |
| | | | | 446/227 |
| 2013/0131553 | A1* | 5/2013 | Clinton-Barnett | A61B 5/1116 |
| | | | | 600/595 |
| 2014/0141950 | A1 | 5/2014 | Greiwe | |
| 2015/0321112 | A1* | 11/2015 | Aboukrat | A63H 33/00 |
| | | | | 446/227 |
| 2016/0067622 | A1* | 3/2016 | Aderka | A63H 33/006 |
| | | | | 446/227 |

* cited by examiner

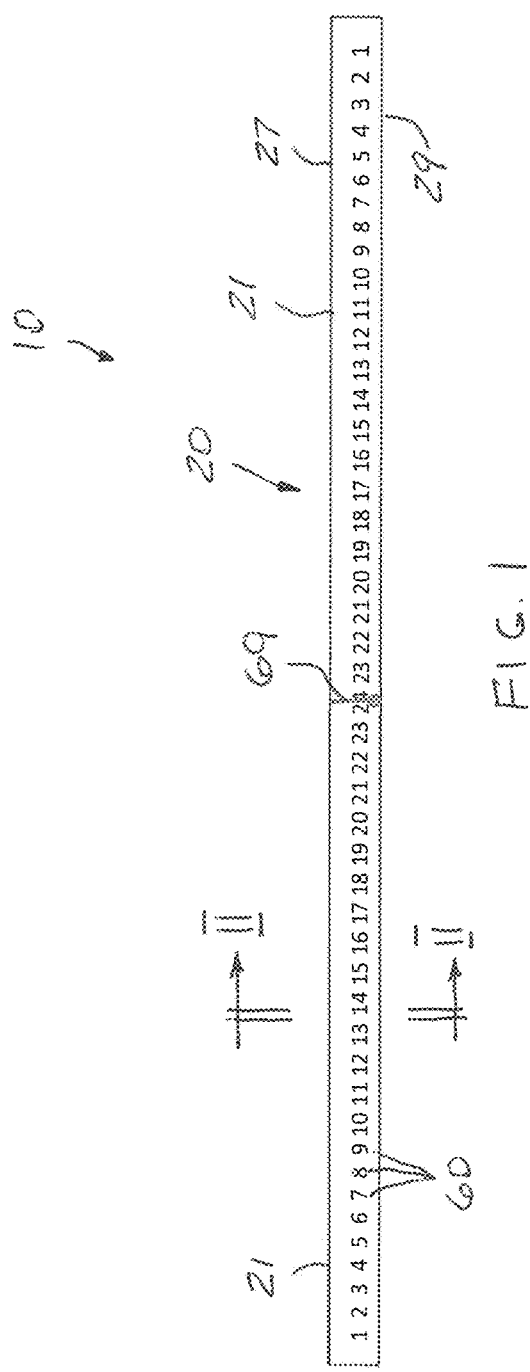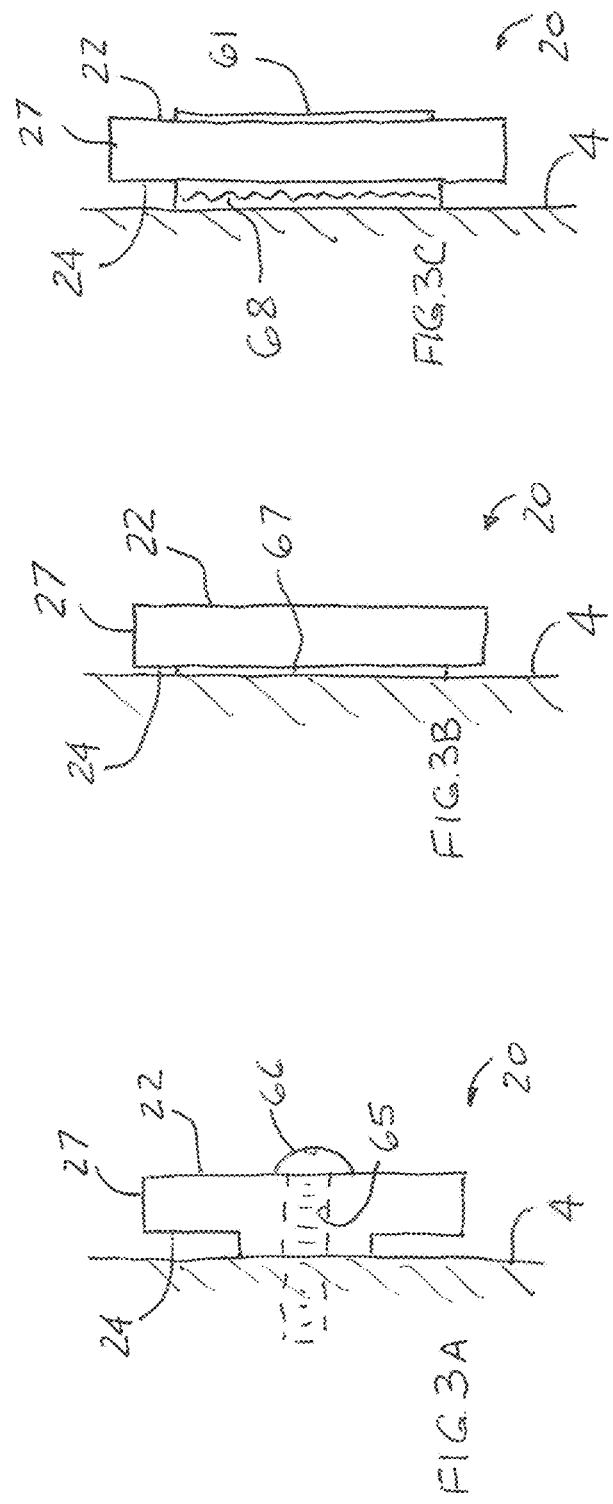

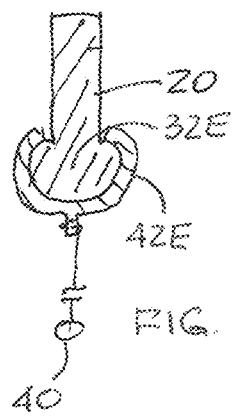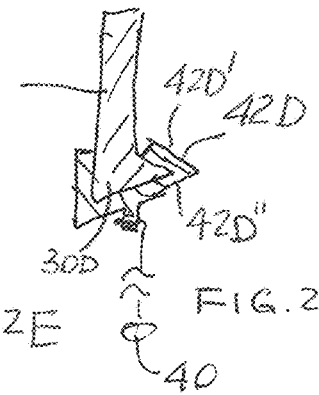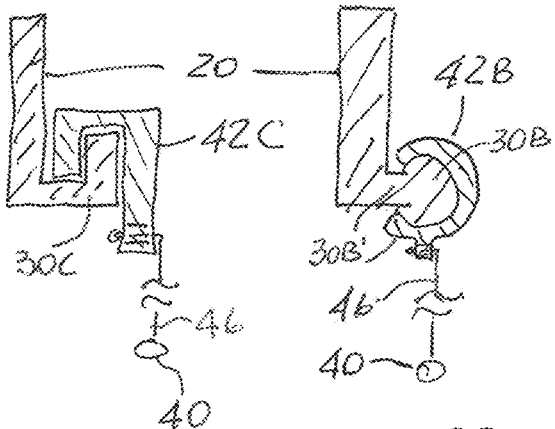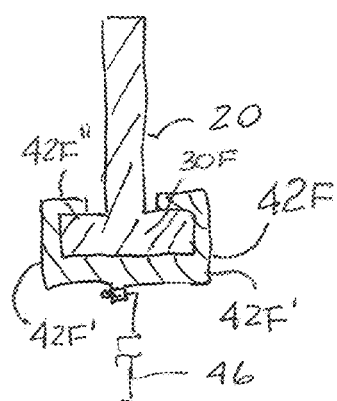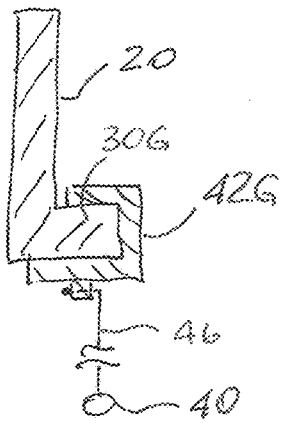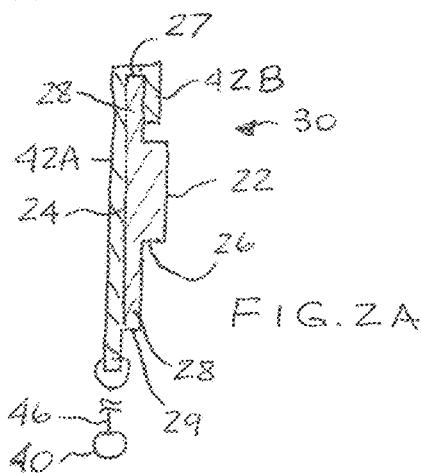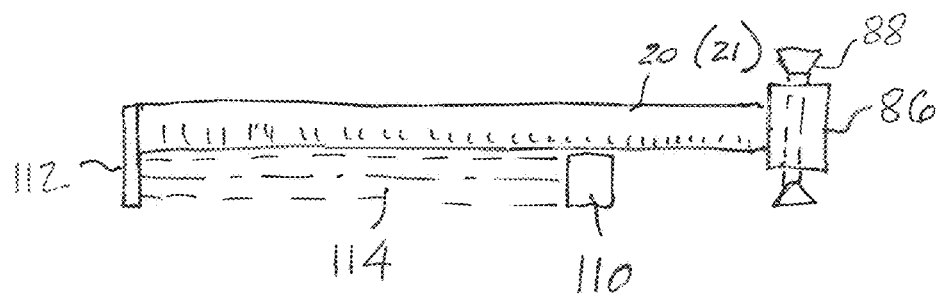

11,064,915 B2

FUNCTIONAL REACH ASSESSMENT DEVICE AND METHOD

CROSS-REFERENCE TO RELATED APPLICATIONS

The present application claims priority from and a benefit of a provisional U.S. patent application No. 62/413,516, tilted "FUNCTIONAL REACH ASSESSMENT DEVICE AND METHOD" and filed on Oct. 27, 2016 by Inventor Norman L. Johnson. The foregoing reference is hereby incorporated herein by reference in their entirety.

STATEMENT REGARDING FEDERALLY SPONSORED RESEARCH AND DEVELOPMENT

N/A

REFERENCE TO SEQUENCE LISTING, A TABLE, OR A COMPUTER PROGRAM LISTING COMPACT DISC APPENDIX

N/A

BACKGROUND

1. Technical Field

The subject matter relates to assessment or management of a medical condition or an impairment. It further relates to devices and methods for assessing functional reach of a patient by a medical practitioner.

2. Description of Related Art

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

An assessment of balance exhibited by a patient can be achieved through functional reach assessment in which the patient generally stands erect and stretches out one or both arms. Patient can be also seated. Patient can be also supported by a health care practitioner by way of a harness. The reach is assessed with a numerical value. Generally, a reach measuring 6 inches or less suggests a predisposition to falling.

Lumbar range of motion is typically measured by a medical practitioner with a goniometer, inclinometer, tape measure or other means. The measuring device is held in place with a strap, tape or manually by the medical practitioner. Each technique requires varying amounts of time for the medical practitioner to properly locate the specific anatomical placement site, place the measuring device and perform the measurement. The measurements are limited in a linear direction and corresponding plane for the motion assessed. The reliability of the medical practitioner range of motion values is related to consistent adherence to proper measuring device specific anatomical positioning.

The limitation encountered with the functional reach test with the patient standing stationary in an erect (orthograde) position is that the test is biased in that the majority of daily functional activities that require reaching are not performed with the shoulder positioned at 90° of flexion (Anterior-Posterior or Sagittal plane, Lateral axis) or abduction (Frontal or Lateral plane, Anterior-Posterior axis).

Furthermore, a potential of the functional reach assessment test has not been explored for use in the assessment and treatment of a low back impairment.

Accordingly, there is at least a need to improve the method of the functional reach assessment.

BRIEF DESCRIPTION OF THE DRAWINGS

The accompanying drawings are incorporated in and constitute part of the specification and illustrate various embodiments. In the drawings:

FIG. 1 illustrates an elevation view of an exemplary device that enables or assists in an assessment or a management of a medical condition in a patient;

FIGS. 2A-2G illustrate exemplary cross-sectional views of the device of FIG. 1 along lines II-II;

FIGS. 3A-3C illustrate elevation views of examples of attaching the device of FIG. 1 to a vertical surface or structure;

FIG. 10 illustrates an elevation view of an exemplary device that enables or assists in an assessment or a management of a medical condition in a patient;

DETAILED DESCRIPTION OF EXEMPLARY EMBODIMENTS

Figure 4:
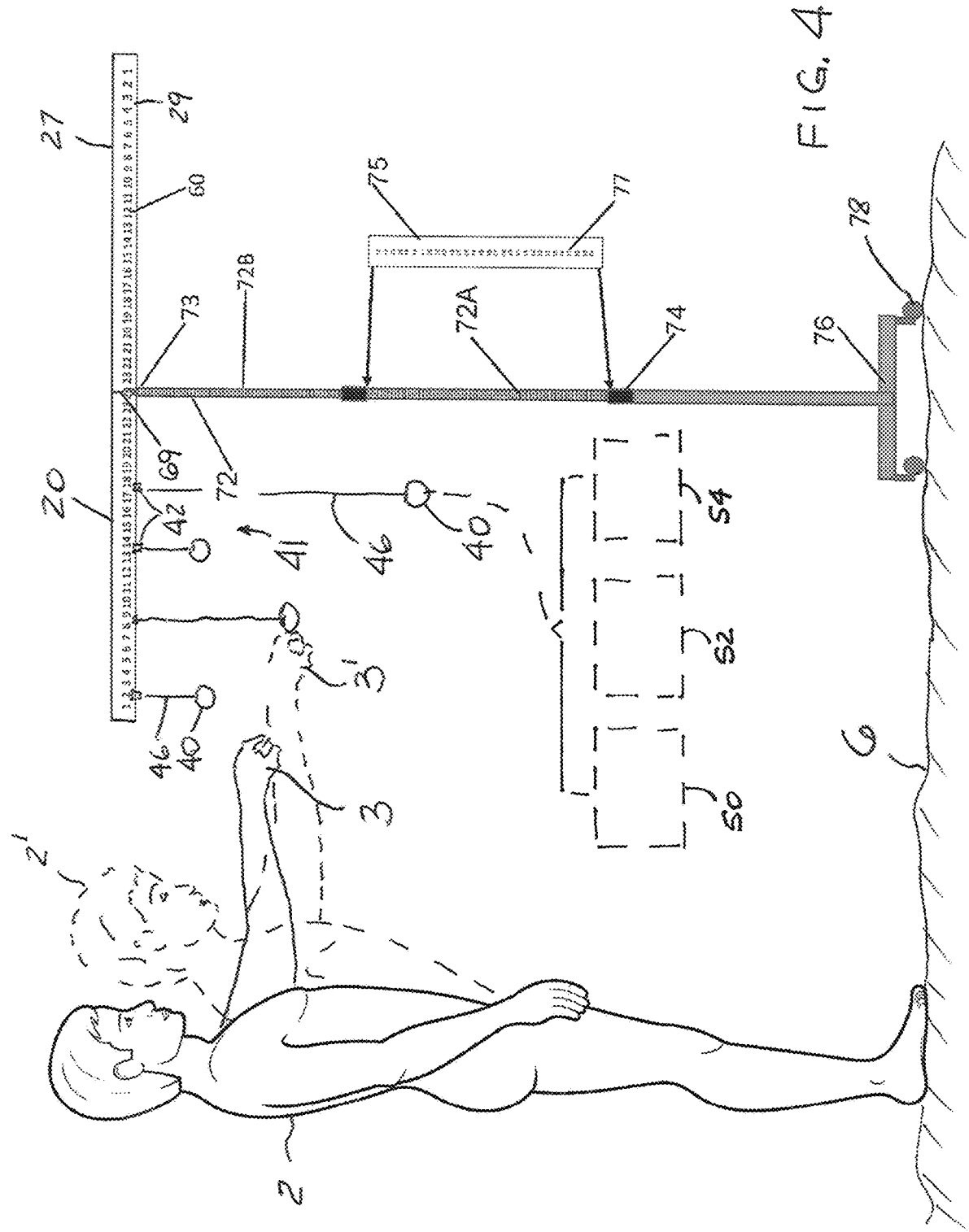
FIG. 4 illustrates an elevation view of an exemplary device that enables an assessment or a management of a medical condition in a patient.

Prior to proceeding to the more detailed description of the present invention, it should be noted that, for the sake of clarity and understanding, identical components which have identical functions have been identified with identical reference numerals throughout the several views illustrated in the drawing figures.

The following detailed description is merely exemplary in nature and is not intended to limit the described examples or the application and uses of the described examples. As may be used herein, the words "example", "exemplary" or "illustrative" means "serving as an example, instance, or illustration." Any implementation described herein as "example", "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure.

References in the specification to "an embodiment", "an exemplary embodiment", an "example" and similar phrases mean that a particular feature, structure, or characteristic described in connection with the embodiment or variation, is included in at least an embodiment or variation of the invention. The phrase "in an embodiment" or similar phrases, as may be used in various places in the specification, are not necessarily meant to refer to the same embodiment or the same variation.

For purposes of description herein, the directional and/or relationary terms such as "upper", "top", "lower", "bottom", "left", "right", "rear", "back", "front", "apex", "vertical", "horizontal", "lateral", "exterior", "interior" and derivatives thereof are relative to each other and are dependent on the specific orientation of an applicable element or article, and are used accordingly to aid in the description of the various embodiments and are not necessarily intended to be construed as limiting. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Furthermore, there is no intention to be bound by any expressed or implied theory presented in the preceding technical field, background, or the following detailed description. It is also to be understood that the specific devices and processes illustrated in the coupled drawings, and described in the following specification, are simply examples of the inventive concepts. Hence, specific dimensions and other physical characteristics relating to the examples disclosed herein are not to be considered as limiting.

The term "or" when used in this specification is not meant to be exclusive; rather the term is inclusive, meaning either or both.

The term "couple" or "coupled", when used in this specification, refers to an indirect or direct physical connection between the identified elements, components, or objects. Often the manner of the coupling will be related specifically to the manner in which the two coupled elements interact.

The term "directly coupled" or "coupled directly," when used in this specification, refers to a physical connection between identified elements, components, or objects, in which no other element, component, or object resides between those identified as being directly coupled.

The term "generally horizontal(ly)" or "generally vertical (ly)" should be also understood to mean respectively horizontally or vertically disposed element or surface but the term does not exclude the possibility of orienting such feature or surface at a small angle relative to respectively absolute horizontal or vertical plane or line.

The terms "removable", "removably coupled", "removably disposed," "readily removable", "readily detachable", "detachably coupled", "separable," "separably coupled," and similar terms, when used in this specification, refer to structures that can be uncoupled, detached, uninstalled, or removed from an adjoining structure with relative ease (i.e., non-destructively, and without a complicated or time-consuming process), and that can also be readily reinstalled, recoupled, or coupled to the previously adjoining structure.

As may be used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

Anywhere the term "comprising" is used, embodiments and components "consisting essentially of" and "consisting of" are expressly disclosed and described herein.

The terms and words used in the following description are not limited to the bibliographical meanings, but, are merely used by the inventor to enable a clear and consistent understanding of the invention. Accordingly, it should be apparent to those skilled in the art that the following description of exemplary embodiments is provided for illustration purpose only and not for the purpose of limiting the subject matter and their equivalents.

It is to be understood that the singular forms "a," "an," and "the" include plural referents unless the context clearly dictates otherwise. Thus, for example, reference to "a component surface" includes reference to one or more of such surfaces.

The particular embodiments of the present disclosure generally provide device and method directed assessment or a management of a medical condition or an impairment.

The particular embodiments of the present disclosure generally provide device and method directed to functional reach assessment.

The functional reach assessment device, may be hereinafter referred to in this document as "device".

In an embodiment, the device is a physical device being configured so that the patient has to reach, with his arm extended, and at least touch if not grasp an object that is configured for a movement in a linear direction. The object is mounted for movement so that the object can be positioned at a desired distance. Alternatively, the patient can move the object. In either approach, a measured numerical value (between starting and ending positions) of the reach or the object movement enables assessment of the patient's mobility or a medical impairment.

Now in reference to FIGS. 1-3C, an exemplary embodiment of such physical device 10 comprises a base member 20, one or more targets 40, markings 60 and coupling members 41. The base member 20 is generally provided as an elongated base member 20, meaning that a length of the base member 20 is greater than a width thereof. The elongated base member 20 comprises a first or front surface 22 and a second or rear surface 24 spaced apart from the first surface 22 to define a thickness of the base member 20. The base member 20 also comprises a top edge 27 and a bottom edge 29, both running along the length of the base member 20. It is not necessary for the surfaces 22 and 24 to be planar surfaces, as illustrated. Nor it is necessary for the surfaces 22 and 24 to be continuous surfaces and voids or protrusions are also contemplated. For example, one or both surfaces 22 and 24 can be adapted with reinforcing ribs (not shown).

Markings 60 are disposed, in a series with each other along the length of the base member 20, on the front surface 22 of the base member 20. The front surface 22 is disposed to face a patient 2 during use of the device 10. However, markings 60 can be optionally disposed on an opposite rear surface 24 or even on both surfaces 22 and 24. The markings 60 comprise a series of numbers either in English or Metric measurement system or both. Essentially, markings 60 define a ruler configuration of the base member 20. The markings 60 may be for example lines, spaced apart from each other to qualitatively assess the reach based on predefined standards. One of such markings 60 can be selected during use of the device 10 to define a starting position. Additional markings 60 are being positioned relative to the starting position to define a range of movement or a stability index. Two sets of markings 60 can be provided for both a left-hand and a right-hand use of the device 10, each set starting at a respective end of the base member 20. When two sets of markings 60 are provided, the elongated member 20 can be adapted with a hinge 69 so that the base member 20 can be folded for storage or transport purposes. In an example, the hinge 69 can be a conventional hinge where the base member 20 is provided as a pair of individual (half) members 21 and each half of the hinge 69 is attached to a respective individual member 21 either by fastening or adhesives. In an example, the hinge 69 can comprise a portion of the base member 20 having a reduced thickness so that the hinge 69 comprises a living hinge. It is further contemplated that the base member 20 can be provided as the pair of half members 21 even when the hinge 69 is not used, with each half member being individually mounted so as to define such base member 20. In other words, it is not necessary for the base member 20 to be a continuous a single piece member.

The markings 60 can comprise both numbers and lines. The device 10 can be used in applications where it is not necessary to measure exact length of the reach. The markings 60 can be disposed on the front surface 22, for example being applied by a paint, or embedded into the thickness of the base member 20, or both embedded into the thickness and painted or provided as a decal. When markings 60 are provided as a decal 61, the decal 61 can be detachably or permanently attached to the front surface 22, for example with an adhesive or by way of an electrostatic charge. Each marking 60 can be provided as an individual decal.

The target 40 can be provided in any shape. The target 40 can be provided as a ball-shaped or spherical member. The target 40 can be a hollow or solid.

The coupling member (or coupling connection) 41 comprises a mounting portion 42 configured to cage a portion of the base member 20. The mounting portion 42 is coupled to the base member 20 so as to at least prevent if not completely eliminate unintended disengagement of the target 40 from the base member 20. The mounting portion 42 can be a clip configured to cage the thickness of the base member 20.

The coupling member 41 also comprise a member 46 that connects a single target 40 with its respective mounting portion 42. The member 46 can be provided in any shape. The member 46 can be any one of a flexible member, a rigid member and a combination thereof.

Each target 40 can be configured to move, in a linear reciprocal motion, along the length of the base member 20 when the patient is required to reach, grasp a selected target or targets 40 or even pull or push the selected target or targets 40 along the length of the base member 20. When the target 40 is configured to move, the device 10 comprises coupling members 41, each coupling member 41 couples a respective target 40 to the base member 20 for a reciprocal linear movement along a length of the base member 20.

Movable coupling between the target 40 and the base member 20 can be illustrated by examples of FIGS. 2A-3G. In the embodiment of FIGS. 2A-2G, the base member 20 may define an elongated rail with each target 40 being configured and mounted on the rail 20 for a reciprocal linear movement thereon in a manner so as to prevent unintended disengagement from the rail 20. Furthermore, the rail 20 can be also adapted with a guide or a guide portion 30 that can protrude or extend from the base member 20.

In an example of FIG. 2A, the guide 30 can comprise a notch 26 in the front surface 22 that runs along the length of the base member 20 and that defines a reduced thickness portion 28 of the base member 20, the reduced thickness portion 28 containing the top edge 27. It is also contemplated that another notch 26 can be provided in the front surface 22 along the bottom edge 29. It is also contemplated that the notch or notches 26 can be provided in the rear surface 24. The mounting portion 42 may be then configured as a J-shaped member 42A to partially cage or partially envelope the thickness portion 28 defined by such notch 26 with a flange 42B of such mounting portion 42 being disposed in the notch 26. In an example of FIG. 2B, the guide 30 comprises a generally cylindrical member 30B that is connected to the base member 20 with a neck 30B'. The flange 42B can be then adapted with a complimentary C-shaped cross-section in a plane normal to the length of the base member 20.

In an example of FIG. 2C, the guide 30 comprises an L-shaped flange 30C. The mounting portion 42C can be then adapted with a J-shaped cross-section in a plane normal to the length of the base member 20.

In an example of FIG. 2D, the guide 30 comprises a flange 30D defines by a pair of inclined surfaces. The mounting portion 42D is adapted with a complimentary mating flanges 42D' and 42D".

In an example of FIG. 2E, the guide 30 essentially comprises a cylindrical member 30E with the mounting portion 42E of the target 40 is adapted with a complimentary shape, which is illustrated as a C-shape in a plane normal to a length of the base member 20. The cylindrical member 30E does not have to be solid and can be provided as a tubular member with a hollow interior.

In an example of FIG. 2F, the guide 30 comprises a flange 30F that defines a T-shaped cross-section of the base member 20 in a plane normal to a length thereof. The mounting portion 42F can be then adapted with a pair of flanges 42F' and a pair of inturned flanges 42F" so as to cage such flange 30F.

In an example of FIG. 2G, the guide 30 comprises a flange 30G that defines an L-shaped cross-section of the base member 20 in a plane normal to a length thereof. The mounting portion 42G can be then configured as having a U-shaped or a J-shaped cross-section in the plane normal to the length of the base member 20.

It would be understood that the examples of FIGS. 2A-2G provide means for moving the target(s) 40 along or on a base member 20.

During use, the device 10 can be provided as a stationary device, being either permanently or detachably mounted or can be provided as a mobile device for ease of transport or positioning at a desired location. Accordingly, the device 10 comprises a means for mounting (supporting) the base member 20 with the targets 40 either in a stationary manner or in a mobile (movable) manner at an elevation above a surface that a patient stands on during the use of the device 10. In either condition, the base member 20 is mounted generally horizontally so that the targets 40 are being suspended in a vertical direction.

In an embodiment, the base member 20 may be secured, either detachably or permanently to a vertical surface 4. Such vertical surface can be part of a wall in an examination room or office. In an example of FIG. 3A, the base member 20 can be directly and securely coupled to the surface 4 with conventional fastener(s) 66 passed through aperture(s) 65 within the thickness of the base member 20. In an example of FIG. 3B, the base member 20 can be coupled to the surface 4 with an adhesive 67. In an example of FIG. 3C, the base member 20 may be attached with a hook and loop fastener 68 positioned on the rear surface 24. In an example, the base member 20 can be suspended either from a vertical or a horizontal surface. The adhesive 67 and the hook and loop fastener 68 can be provided as a single continuous member or two or more segments spaced apart with each other along the length of the base member 20. Thus, the examples of FIGS. 3A-3C provide a means for attaching the base member 20 or the device 10 to a vertical surface or structure.

In an embodiment, the base member 20 can be supported, in a stationary manner, by a support 70.

Now in a reference to FIGS. 4-12, the device 10 is provided as a mobile device. In this embodiment, the base member 20 can be mounted at or near a top end 73 of a vertical support member 72. The vertical support member 72 can be provided as a fixed length member or can be provided with one or more adjustable portion 72A, 72B as an adjustable length member of a telescopic type, for example fitted with height locking collars 74. Furthermore, the vertical support member 72, provided in sections, may have one or more sections, such as portion 72A and/or 72B adapted with markings 77 defining a ruler 75. The ruler 75 expedites positioning of the base member 20 in a vertical direction. Although such position is generally at a shoulder level of the patient 2, it can be higher or lower to introduce additional effort of reaching or lounging at an incline rather than in a straight line and even bending at the waist line. Although the vertical support member 72 has been shown herein as comprising three sections, more or less sections are contemplated herewithin. The vertical support member 72 with the base member 20 and ball-shaped (or other shaped) targets 40 can be configured to upstand on a wheeled base 76 with wheels 78. The wheeled base 76 can be also provided as a tripod. It is to be understood that the targets 40 are configured as a linear array on the elongated base member 20.

In either of the above described embodiments, the targets 40 can be suspended at same or different distances from the bottom edge 29 of the base member 20 and, consequently, at same or different heights from a surface 6 that the patient 2 is standing or sitting on. In this embodiment, the patient 2 will generally stand or sit at one end of the base member 20 and face the vertical support member 72. During assessment, the patient 2 will reach toward the vertical support member 72. The end of the base member 20 that the patient 2 will stand or sit at is determined based on the hand that the patient 2 will reach with. Generally, the patient 2 will stand or sit so that his/her arm is in close proximity to the base member 20. In other words, if the patient 2 will reach with his/her left arm, the patient 2 will stand or sit at the left of FIG. 4. If the patient 2 will reach with his/her right arm, the patient 2 will stand or sit at the right of FIG. 4.

Figure 5:
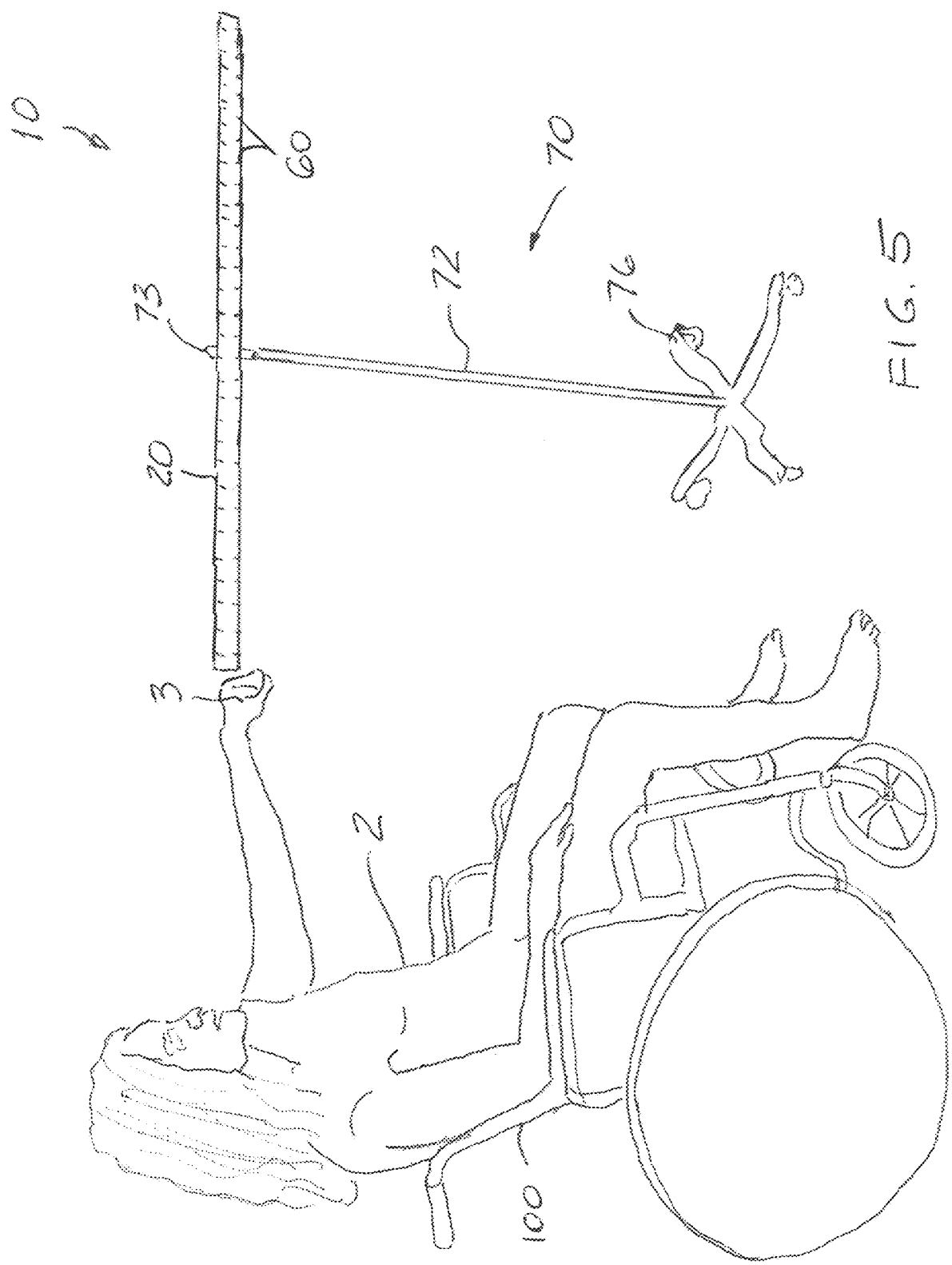
FIG. 5 illustrates an elevation view of an exemplary device that enables an assessment or a management of a medical condition in a patient being seated.
Figure 6:
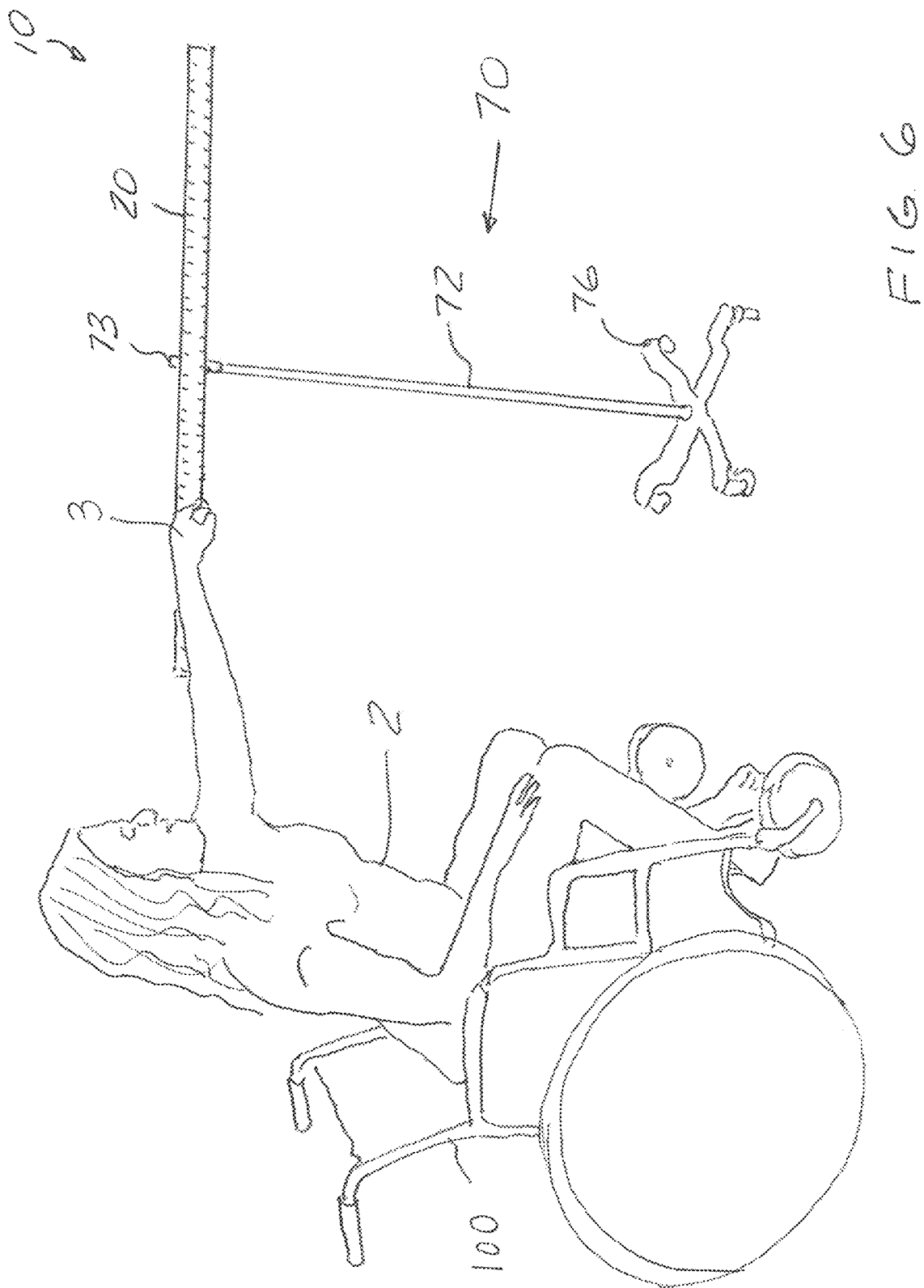
FIG. 6 illustrates an elevation view of the exemplary device of FIG. 5 with the patient leaning forward.

In an example of FIGS. 5-6, the device 10 can be provided without the suspended targets 40.

The limitation encountered with the functional reach test with the patient 2 standing stationary in an erect (orthograde) position is that the test is biased in that the majority of daily functional activities that require reaching are not performed with the shoulder positioned at 90° of flexion (Anterior-Posterior or Sagittal plane, Lateral axis) or abduction (Frontal or Lateral plane, Anterior-Posterior axis). The disclosed embodiments for the functional reach test device 10 can measure forward, backward and lateral arm movement distance which can be recorded when the patient 2 needs to take a step to maintain standing balance.

The incorporation of a target or targets 40 at various heights and distances requires the patient 2 to maintain standing or seated (if performed in a sitting position) balance while using visual tracking to reach or lunge toward the targets 40 while being instructed, monitored and/or supervised by a medical professional. In other words, the device 10 is designed to assess a medical condition of the patient 2 in a manner where the patient 2 does not change the initial position of the feet and waist line. However, stepping action by the patient 2 is also contemplated, particularly when the patient 2 is standing.

Figure 7:
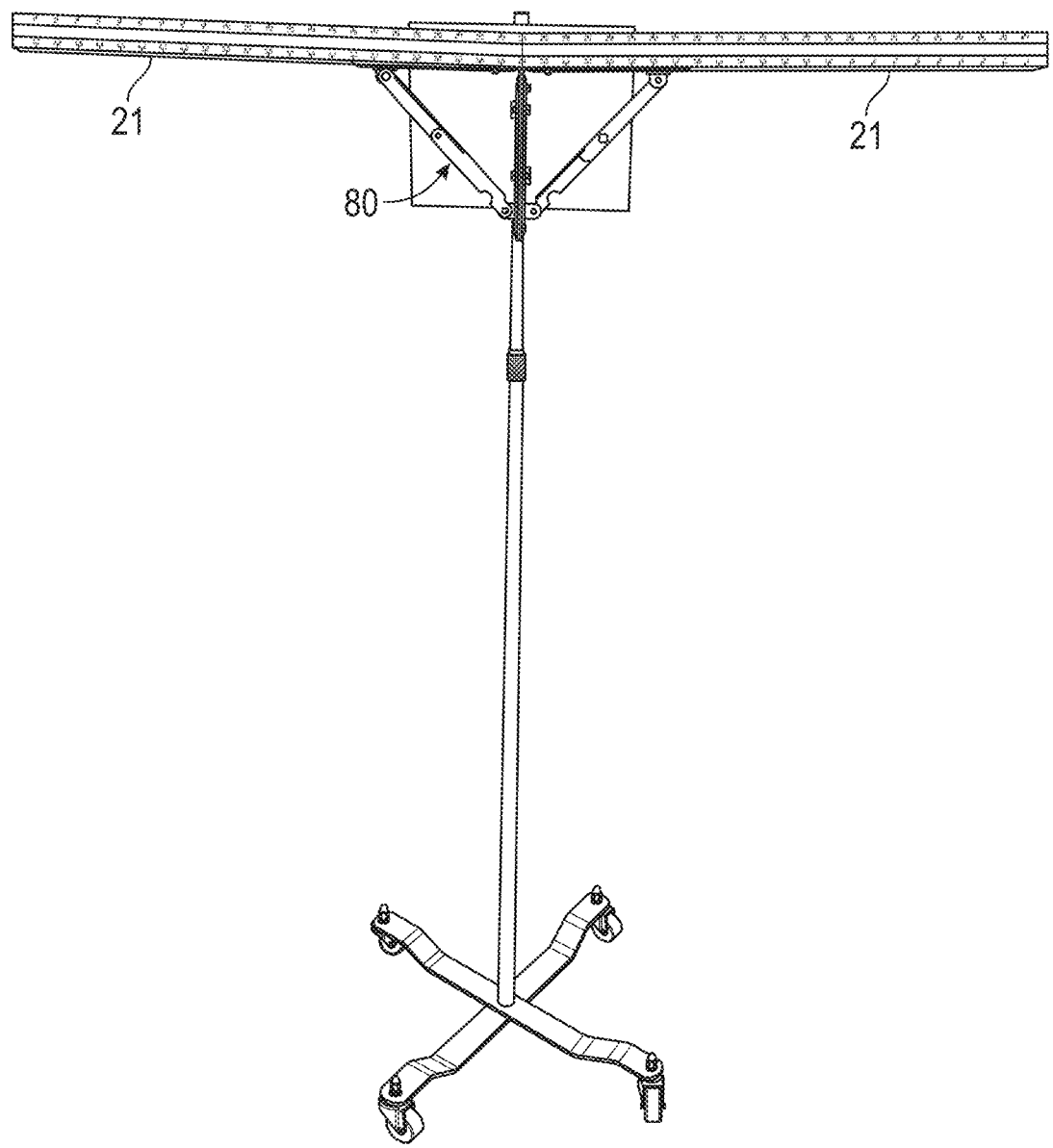
FIG. 7 illustrates an elevation view of the device of FIGS. 4-6 adapted with a scissor mechanism.
Figure 8:
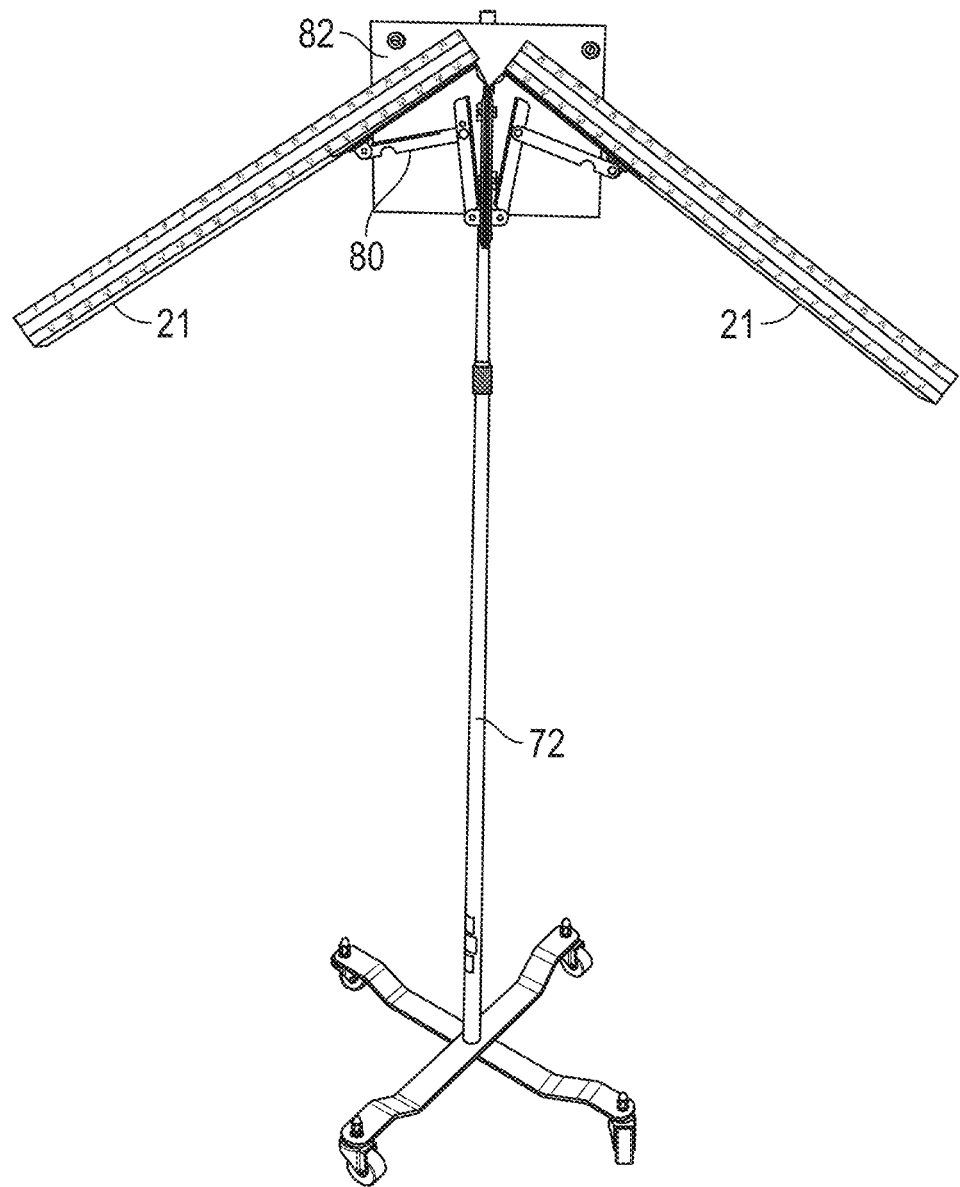
FIG. 8 illustrates an elevation view of the device of FIG. 7 being in an intermediate position.
Figure 9:
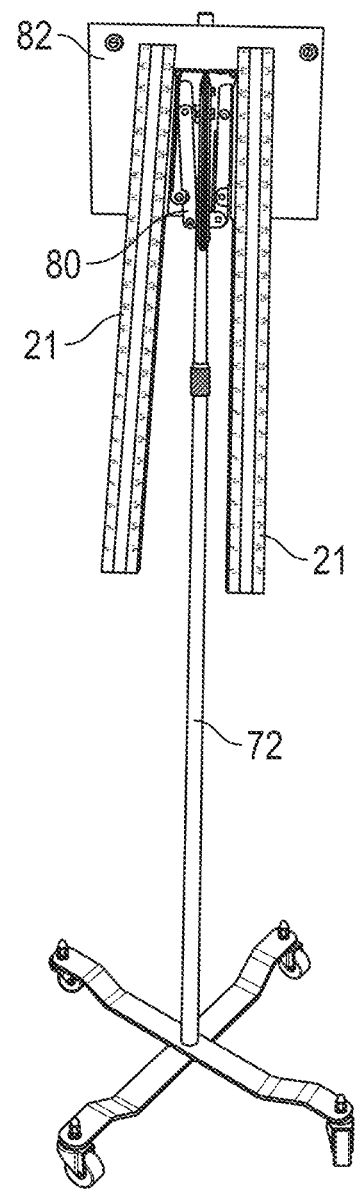
FIG. 9 illustrates an elevation view of the device of FIG. 7 being in one terminal position.

In an embodiment of FIGS. 1 and 7-9, the base member 20 can be configured or provided as a pair of half portions 21 that could be identical with each other, except for a direction of markings 60. In a further reference to FIGS. 7-9, there is also illustrated a scissor-type mechanism 80 that has portions thereof being rigidly secured to each of the half portions 21. The scissor-type mechanism 80 is configured to move both half portions 21 between an operable first position in FIG. 7, wherein the base member 20 is disposed generally horizontally and a folding second position in FIG. 9, wherein the half portions 21 are either disposed generally parallel to the vertical support member 72 or at some incline to the vertical support member 72. As it can be seen in FIG. 8, the half portions 21 can be maintained in an intermediate position anywhere between the first and second positions. In this example, the device 10 can also comprise a mounting member 82 also having scissor-type mechanism 80 being attached to. Thus, the method of functional reach assessment may also comprise providing the base member 20 in two half portions 21 and moving the half portions 21 between an operable and folded positions. The scissor-type mechanism 80 may be replaced with the above described hinge 69 adapted with a locking feature. FIGS. 7-9 also illustrate that the device 10 can be simply positioned next to a movable privacy partition or a screen that separates different examination areas within the same examination room. Thus, the mobile device 10 is configured so as to not require any rigid and/or stationary structures.

In an example of FIG. 10, the base member 20 may be provided as a single half portion 21. Such single half portion 21 may be mounted in a stationary position or configured for a rotating movement. When the half portion 21 is configured to rotate, the single half portion 21 can have one end thereof attached to a housing 86 that is adapted with a pivot 88. The housing 86 or the pivot 88 can be attached to a structure. The structure can be a stationary surface, such as the wall surface 4, or the above described vertical support member 72.

In an example, the base member 20 may be mounted, on a stand, for example such as a tri-pod.

In an example, the base member 20 may be mounted to a post 206 of a patient analysis system 200 described in U.S. Pat. No. 7,526,071 issued to Drapeau on Apr. 8, 2009 and whose relative teachings are incorporated by reference herein.

In an example, the base member 20 may be configured to attach onto a vertical sliding rail of Exercise Wall Station as sold under the TheraBand® brand. The base member 20 will be then configured/adapted for a linear reciprocal motion in a vertical direction. In other words, the device 10 can be configured as an accessory for the Exercise Wall Station as sold under the TheraBand® brand. Furthermore, the above described vertical support member 72 can be configured as a freestanding sliding rail and the base member 20 may be similarly configured so that the base member 20 moves (slides) linearly along a length of the vertical support member 72.

In an embodiment, the markings 60 can be provided as two sets of numerals, each having a lower number at one free end of the base member 20 and converging toward the middle of the base member 20.

Such two sets of numerals are advantageous in that both Metric and/or English System the measurement may be obtained. Both measurement systems can be used, for example each measurement being disposed close to one longitudinal edge of the base member 20, since Metric measurement is routinely used in all countries except the United States, Liberia and Myanmar. With this inclusion of both sets of measurements, the functional reach device may be used globally. Additionally, traditional measurement scale devices run the numbers in a left to right direction. Thus, when functional reach activities are performed on the right side of the measurement scale going to the left, the lower number obtained must be subtracted by the high number starting point. With the measurement scale running from left to right and right to left directions, the distance of the functional reach movement is immediately available which eliminates the need for subtraction whereby reducing potential calculation errors. Also, a reach indicator on the device is easily advanced to the position on the unit arm to accurately measure and record the reach distance moved. Another advantage is the incorporation of numbers to measure the vertical starting height of the functional reach device. The ability to record this information increases the reliability of future patient 2 assessment.

To perform functional reach assessment in the embodiments of FIGS. 1-4, the patient 2 can stand normal to the base member 20 with the fisted hand 3 extending along the length of the base member 20. The medical practitioner 8 may move one target 40 to touch the fist of the patient 2 and record the corresponding marking 60 as a starting marking or position. In other words, it is not necessary that the fist is positioned at a zero mark. The patient 2 then leans forward with the fisted hand 3 extended into the position 2' and attempts to or reaches toward one or more targets 40 depending on a length of the reach. The patient can touch and even grasp the target 40. When the member 46 is a rigid member, the patient 2 can grasp the target 40 in the starting position and move the target 40 by way of its mounting portion 42 along the length of the base member 20 into a position denoted by 2', until the patient 2 cannot reach any longer. The medical practitioner 8 then records the corresponding marking 60 and calculates an actual reach as a dimensional difference between the starting and ending markings 60. It is not necessary that the patient 2 touches the target 40 and the assessment or management can be carried out by a relative position of the fisted hand 3 next to a specific target 40.

To perform functional reach assessment in the embodiments of FIGS. 5-6, the patient 2 sits, for example in a wheelchair 100, with the fisted hand 3 extended along the length of the base member 20. The medical practitioner 8 records the corresponding marking 60 as a starting marking or position. In other words, it is not necessary that the fist is positioned at a zero mark. The patient 2 then leans forward, as is best shown in FIG. 6, with the fisted hand 3 extended into the position 2' and reaches until the patient 2 cannot reach any longer. The medical practitioner 8 then records the corresponding marking 60 as the ending marking or position and calculates an actual reach as a dimensional difference between the starting and ending markings 60. It would be understood that FIGS. 5-6 illustrate an embodiment where the device 10 is provided without the targets 40 and the coupling members 41. However, it is contemplated that the device 10 in the embodiments of FIGS. 5-6 can be adapted with the targets 40 with the method being similar to the method described in a reference to FIG. 4, except for the sitting position of the patient 2. Thus, the device 10 can be used by patients who are unable to stand or have difficulty standing during a duration of the assessment routine. In other words, the device 10 can be used with patients 2 who either temporarily or permanently lost control of their lower extremities. Although the wheelchair 100 is shown as being oriented toward the vertical support member 72 (or to the right in FIGS. 5-6.), it may be oriented away from the vertical support member 72 (or to the left in FIGS. 5-6). The method will then comprise positioning the wheelchair 100 (or any other chair) adjacent the device to carry out reaching assessment.

Figure 11:
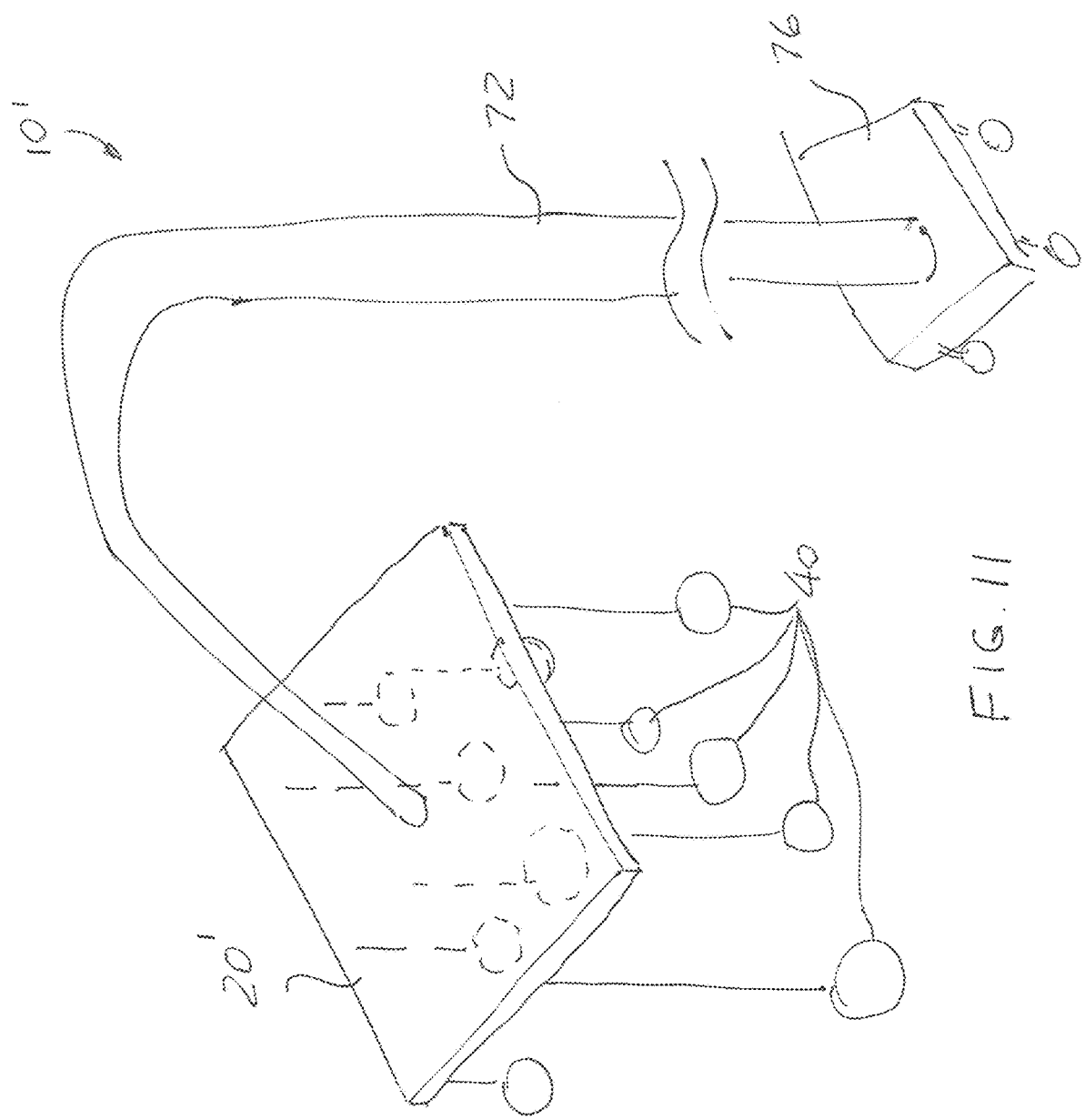
FIG. 11 illustrates a 3D view of an exemplary device that enables or assists in an assessment or a management of a medical condition in a patient.

Now in a reference to FIG. 11, therein is illustrated a device 10' that enables or assists in an assessment or a management of a medical condition or an impairment in a patient and that comprises a base member 20', a support member 72 that couples to the base member 20' and that supports the base member 20' above a surface that the patient 2 stands or sits on during the use of the device 10', and an array of targets 40 suspended from the base member 20', where some targets 40 from the array of targets 40 are being disposed at different elevations relative to remaining targets 40 from the array of targets 40. In other words, the device 10' is configured to provide a three-dimensional array of targets 40. It is also contemplated that the device 10' can comprise two or more elongated base member 20 disposed next to each other on the base member 20' or integrated into a unitary one-piece construction.

In either configuration of the device 10 or 10', the targets 40 in the array of targets 40 can be provided in a plurality of colors to develop auditory and sensory skills.

Figure 12:
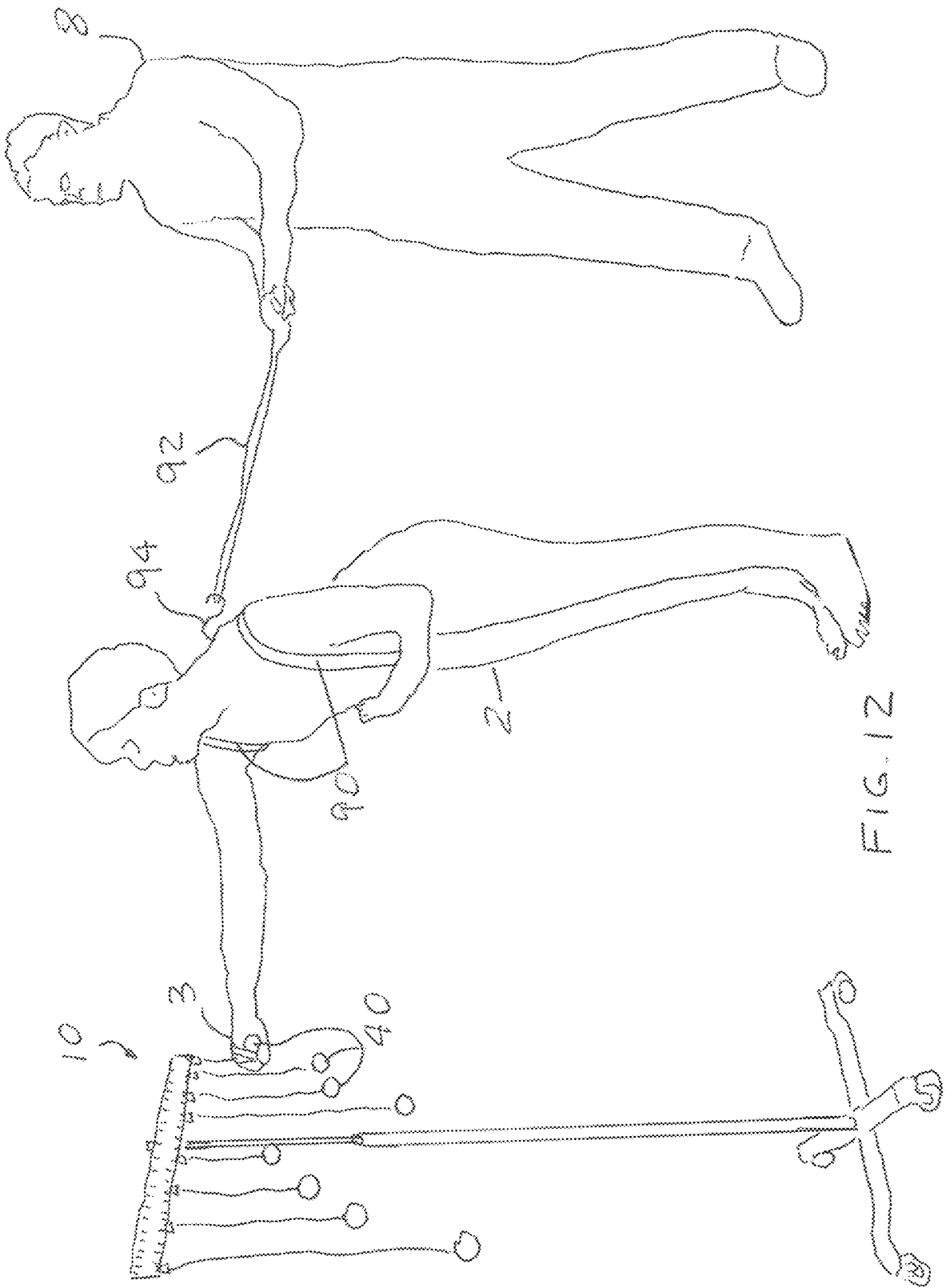
FIG. 12 illustrates use of a harness and a resistance member in a combination with the device of FIG. 4 or FIG. 11.

Now in a reference to FIG. 12, the device 10 or 10' can be also used in a combination with a harness 90 worn by the patient during use of the device 10 or 10'. The harness 90 can be held by the medical practitioner 8 to assist patient 2 in maintaining stability and preventing a fall condition. Furthermore, the patient 2 can be challenged with an additional resistance during the assessment, treatment or exercise by way of a resistance inducing member 92, for example such as a spring or an exercise band. In this embodiment, the harness 90 will have a connection 94 with one end of the resistance inducing member 92. Such connection can be a hook or a carabineer. When the patient 2 is to exercise flexors, the resistance inducing member 92 will be connected to the front of the harness 90. When the patient 2 is to exercise extensors, the resistance inducing member 92 will be connected to the back of the harness 90. Furthermore, FIG. 12 illustrates an embodiment where the elongated member 20 is positioned across the torso of the patient 2 so as to promulgate reaching with the fisted hand 3 across the torso, while maintaining the feet in a stationary position.

In either configuration of the device 10 or 10', one or more targets 40 can be provided with a hollow interior and with an electronic circuit 50 and a light emitting member 52 disposed within the hollow interior, where the light emitting member is responsive to actuation of the circuit by a motion of the target 40 or by a patient touch to emit light.

In either configuration of the device 10 or 10', one or more targets 40 can be provided with a hollow interior and with an electronic circuit 50 and a sound emitting member 54 responsive to actuation of the circuit by a motion of the target 40 or by a patient touch to emit sound.

The device 10 or 10' of any of the above described embodiments can be utilized for evaluation and training for medical conditions and surgery where a balance impairment increases the risk of falling which may result in additional injuries. These medical conditions include but are not limited to: amputations, brain injury, cerebral vascular accident, diabetic neuropathy, multiple sclerosis, Parkinson's Disease, total knee replacement, total hip replacement, spinal cord injury and vestibular disorders. For patients 2 that are unable to move to the standing position or may be wheelchair bound the device 10 of any of the above described embodiments can be adjusted to accommodate seated evaluation and training.

Muscles provide dynamic stability and control in both standing and seated positions. Neurological and/or muscular impairments may inhibit normal trunk and/or limb body movement necessary to perform patient 2 specific functional activities. Muscles providing stability of the cervical spinal area include: sternocleidomastiod, scalene, levator scapulae, upper trapezius, erector spinae, rectus capitis anterior and lateralis and longus colli. Muscles providing stabilization of the lumbar spine area include: rectus abdominis, external and internal obliques, quadratus lumborum (lateral portion), erector spinae, iliopsoas, transversus abdominis, multifidus, quadratus lumborum (deep portion) and deep rotators.

Low back pain ranks second as a frequently treated medical problem and is only surpassed by cold and flu. An episode of back pain may cause impairment resulting in limitations of bending and reaching movements that are requisites to perform functional activities. Accordingly, the device 10 or 10' can be used for a non-surgical management of a low back impairment in a patient.

In one non-limiting example, a method of a non-surgical management of a low back impairment in a patient can comprise the steps of providing a device comprising a support member, a base member mounted on the support member, and a linear or a two-dimensional array of targets suspended by coupling members from the base member, some targets from the linear or two-dimensional array of targets are being disposed at different elevations relative to remaining targets from the linear or two-dimensional array of targets. Then, positioning the device in front of or next to the patient or positioning the patient in front of the device. Reaching, by the patient having his/her arm extended, in a direction of a target or targets in the array of targets. Then, observing, by a medical practitioner, the target or targets reached or not reached by the patient. Next, determining, by the medical practitioner, a degree of the low back impairment based on position of the target or targets reached or not reached by the patient. Then, prescribing, by the medical practitioner, based on the degree of the low back impairment, an exercise and/or therapy regimen promulgating improvement in the low back impairment. In this embodiment, the device provides a consistent and accurate measure of the patient condition and/or recovery progress.

The device 10 is adaptable for the evaluation and treatment of various medical afflictions. One example of a method of rehabilitation comprises the incorporation of balance training in a patient who has sustained a brain bleed or stroke. This medical condition may leave the patient with hemiparesis or paralysis on one side of the body and visual neglect on the affected side of the body. After completion of the functional reach assessment to identify patient deficits, the functional reach device 10 can be used in either the standing or seated position to have the patient reach in forward and lateral directions with objects at various heights and distances. The patient 2 can perform these activities from a position either directly in front of the functional reach device 10 or at the side of the functional reach device. The patient would perform the movement upon receiving a verbal command from the medical professional. The movement incorporates both visual and balance training components. Positions, repetitions and device height can be noted. The functional reach device permits 10 the incorporation of diagonal reaching at different heights.

In a further reference to FIG. 10, a target 110 is mounted to move linearly relative to the base member 20 in an accordance with any of the above examples of the mounting portions 42. In this embodiment, the device 10 is adapted with a stop member 112 and a spring 114 that is connected at each end thereof respectively to the stop member 112 and the target 110. In this embodiment, the patient 2 will push the target 110 against the resistance of the spring 114. Although the base member 20 in FIG. 10 is shown as a half portion 21, it can be provided as the full base member with either one or two targets 110, stops 112 and springs 114 and/or be also adapted with targets 40.

Figure 13:
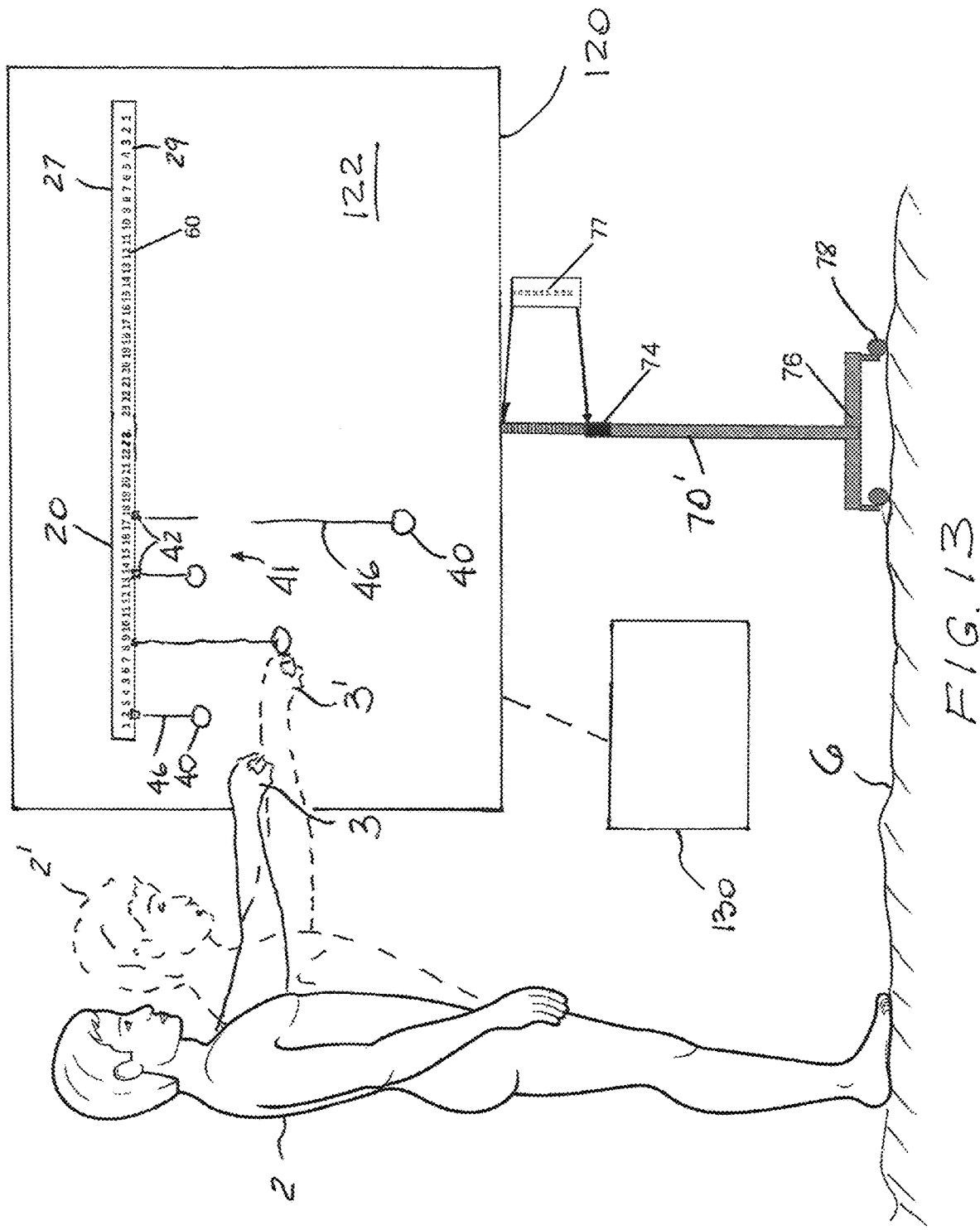
FIG. 13 illustrates an elevation view of an exemplary method for assessing or managing of a medical condition in a patient.

Now in a reference to FIG. 13, therein is shown an embodiment of at least a method of assessing or managing a medical condition or an impairment that provides a display 120 for an interactive functional reach assessment or management of the impairment. The display 120 can be a monitor connected to a computing device 130 with hardware and software components associated with computing devices. The computing device 130 can be a computer or any other electronic device configured to control operation of the display 120. Such computing device 130 can be a mobile computing device that comprises communication, either wired or wireless, with a remotely disposed display 120.

A mobile computing device may refer to any device having a processing system and a mobile power source or supply, such as one or more batteries, for example. Examples of a mobile computing device may include a laptop computer, tablet, touch pad, portable computer, handheld computer, palmtop computer, personal digital assistant (PDA), cellular telephone, combination cellular telephone/PDA, television, smart device (e.g., smartphone, tablet or smart television), mobile internet device (MID), messaging device, data communication device, and so forth. Examples of a mobile computing device also include computers and/or media capture/transmission devices configured to be worn by a person, such as a wrist computer, finger computer, ring computer, eyeglass computer, belt-clip computer, arm-band computer, shoe computers, clothing computers, and other wearable computers. In various embodiments, for example, a mobile computing device may be implemented as a smart phone capable of executing computer applications, as well as voice communications and/or data communications.

The display 120 can be configured to display images of the above described markings 60 with the image of the base member 20 and display the targets 40 with or without images of the coupling members 41. In this example, the assessment or management of a medical condition or an impairment can be carried in accordance with above described method embodiments, except for replacing the support 70 with the display 120. In an example, the display 120 can be also configured to display images of the markings 60 without the outline image of the base member 20. In an example, the display 120 can be configured as a touch sensitive portion. In this example, the patient 2 may touch the front 122 of such display 120 with his/her fist and move the fist, in a linear direction, along the surface of the display 120 and/or bend at the waistline while reaching. When the patient 2 moves his/her fist, the fist can maintain a contact with the front 122. The length of the contact and/or a reach angle from the starting position may remain visible on the display 120. A distance and/or angle of the reach can be displayed, in any units of length, on the display 120, can be displayed remotely at a computing device 130 or can be measured based on numerical values provided by the images of the markings 60. In an example, the display 120, configured as a touch-sensitive display, can be operable to simply dispose the targets 40 either at the same or different elevations in the vertical direction.

The display 120 can be mounted onto a vertical surface, for example such as the wall 4, disposed on a horizontal surface, for example such as a top surface of a desk (not shown) or supported on a support 70', for example being the support 70 adapted for attachment to display 120, with or without the ruler 75 and/or markings 77.

The above described images can be projected from a projector (not shown) onto a vertical disposed surface. Such surface can be the above described wall 4. Or the display 120 of FIG. 12 can be provided as a (projector) screen.

The patient 2 can be still adapted to wear the harness 90 of FIG. 12.

Figure 14:
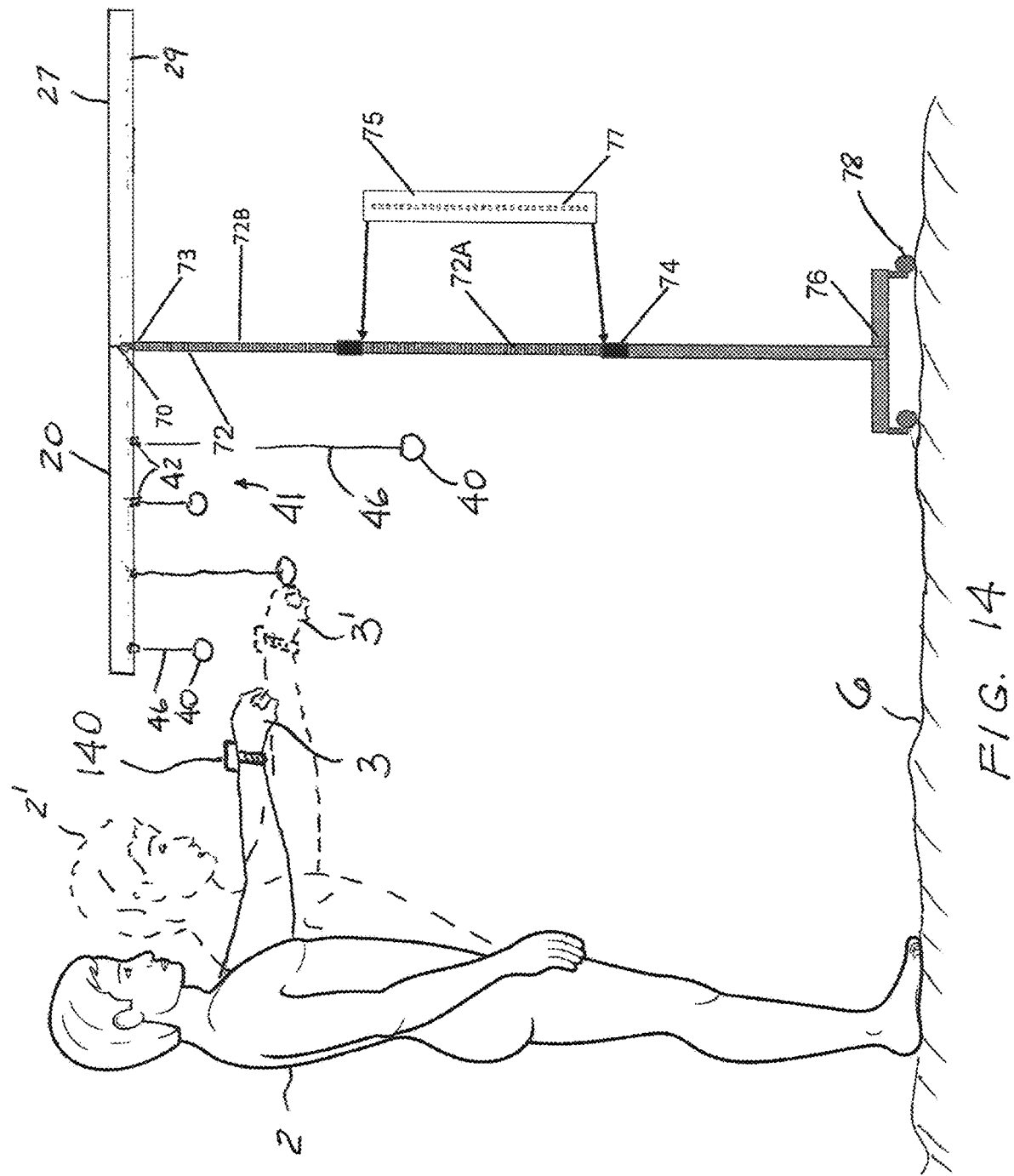
FIG. 14 illustrates an elevation view of an exemplary method for assessing or managing of a medical condition in a patient.

Now in a reference to FIG. 14, a method of assessing or managing a medical impairment in the patient 2 can comprise the steps of providing a wearable device 140 comprising at least a tilt sensor and a distance measurement device; attaching the wearable device 140 to an upper body portion of the patient 2; moving the upper body portion through one or more preselected motions; and measuring at least one of a bend angle of the upper body portion and a distance traveled by the wearable device during a movement of the upper body portion through the one or more preselected motions, where angular and/or linear movement results characterize the medical impairment. In an example, the wearable device is a smartwatch 140 worn on a wrist of the patient 2 during the movement of the upper body portion. The smart watch 140 can be of a type as disclosed in U.S. Pat. No. 8,896,526 A2 issued to Park on Nov. 25, 2014 and/or of the type as disclosed in US Pub. No 2015/0238159 A1 published to Subramaniam on Aug. 27, 2015 and whose teachings are incorporated in their entirety by reference. It would be understood, that the smartwatch of Park will be programmed to carry out the above described method. The method can comprise a step of displaying angular and/or linear movement results on a display in the wearable device 140 and/or a step of communicating the angular and/or linear movement results to a remote location, for example such as computing device 130 with its own display, and a step of displaying the angular and/or linear movement results on a display in the remote location. The step of moving comprises a step of establishing a starting position with the wearable device 140.

In an example, the wearable device can be a smart eyewear worn on a head of the patient during the movement of the upper body portion. In an example, such smart eyewear can be a type as disclosed in US Pat. Pub. No. 2014/029882 A1 published on Oct. 13, 2016 and whose teachings are incorporated in their entirety by reference.

In an embodiment, a method of assessing or managing a medical impairment in a patient can comprise a step of providing a hand-held distance and angle measuring device. Such hand-held distance and angle measuring device can be of the type as disclosed in U.S. Pat. No. 9,753,135 B2 issued to Bosch on Sep. 5, 2017 and whose teachings are incorporated in their entirety by reference. Then, holding the device by a hand of the patient during an assessment or a management of the medical impairment. Next, moving the hand through one or more preselected motions. And measuring at least one of a travel angle of the device and/or a distance traveled by the device during a movement of the hand through the one or more preselected motions.

In an embodiment, a functional reach assessment device comprises an elongated base member; markings disposed on one surface of the elongated base member; and targets mounted on the elongated base member for a reciprocal linear movement along a length of the elongated base member.

In an embodiment, the device 10 is a free standing and does not depend upon a wall for support, it is portable and adaptable to various testing and treatment environments.

In an embodiment a method of assessing or managing a medical condition in a patient comprises a rotational component where the patient reaches across the body and a bending component where the patient leans forward or backward while reaching. The rotational and bending components can be combined.

In an embodiment, the presented device allows a medical practitioner an efficient approach to accurately assess lumbar motion and deliver a challenging treatment regimen.

The incorporation of a target or targets at various heights and distance requires the patient to maintain standing or seated (if performed in a sitting position) balance while using visual tracking to reach or lunge toward the targets while being instructed by a medical professional.

In an embodiment, a method of assessing or managing a medical condition or an impairment in a patient is performed while feet of the patient remain in a stationary position.

In an embodiment, a device that enables or assists in an assessment or a management of a medical condition or impairment in a patient comprises an elongated base member comprising a pair of surface spaced apart from each other to define a thickness of the elongated base member; markings disposed on one surface from the pair of surfaces of the elongated base member along a length of the elongated base member; targets disposed, during use of the device, below a bottom edge of the elongated base member; and coupling members, each coupling member couples a respective target from the targets to the elongated base member for a reciprocal linear movement along the length of the elongated base member.

A feature of this embodiment is that each coupling member comprises a mounting member configured to cage a portion of the elongated base member; and a member that connects the respective target to the mounting member.

A feature of this embodiment is that the elongated base member comprises a pair of members and wherein the device comprises a hinge coupling the pair of half members therebetween.

A feature of this embodiment is that the device can further comprise a means for supporting the elongated base member at an elevation above a surface that a patient stands or sits on during the use of the device.

A feature of this embodiment is that the means comprises a support member that is disposed vertically.

A feature of this embodiment is that the support member comprises adjustable portions.

A feature of this embodiment is that the device can further comprise a base so that the support member is mounted in a free-standing manner, the elongated base member being stationary mounted at a top free end of the support member.

A feature of this embodiment is that the base comprises a tri-pod.

A feature of this embodiment is that the support member comprises a rail, the elongated base member being mounted, in a generally horizontal direction, on the rail for a reciprocal linear movement along the rail in a vertical direction.

A feature of this embodiment is that the means comprises one or more apertures through the thickness of the elongated base member and one or more fasteners passed through the one or more apertures to engage a structure.

A feature of this embodiment is that the means comprises one or more fasteners on another surface from the pair of surfaces of the elongated base member being opposite to the one surface.

A feature of this embodiment is that the means comprises a pivot between one end of the elongated base member and a structure so that the elongated base member pivots in a generally horizontal plane.

A feature of this embodiment is that the base member is configured as a pair of half portions and wherein the means comprises a scissor mechanism that comprises portions thereof being rigidly secured to each of the pair of half portions, the pair of half members being configured to move between an operable first position where the base member is disposed generally horizontally and a folding second position where the half portions are either disposed generally parallel to the vertical support member or at some incline thereto the vertical support member and can be maintained in an intermediate position anywhere between the first and second positions.

A feature of this embodiment is that device further comprises a harness worn by the patient during use of the device, the harness having a connection with a resistance inducing member.

A feature of this embodiment is that device further comprises a harness worn by the patient during use of the device, the harness being held by a medical practitioner during use of the device.

In an embodiment, a device that enables or assists in an assessment or a management of a medical condition or impairment in a patient comprises a support member disposed vertically during use of the device; an elongated base member comprising a pair of surface spaced apart from each other to define a thickness of the elongated base member, the elongated base member being mounted in a generally horizontal direction at or adjacent a top end of the support member; markings disposed on one surface from the pair of surfaces of the elongated base member along a length of the elongated base member; targets disposed, during use of the device, below a bottom edge of the elongated base member; and coupling members, each coupling member couples a respective target from the targets to the elongated base member for a reciprocal linear movement along the length of the elongated base member.

In an embodiment, a device that enables or assists in an assessment or a management of a medical condition or impairment in a patient comprises a base member; a support member that couples to the base member and that supports the base member above a surface that a patient stands or sits on during the use of the device; and an array of targets suspended from the base member, some targets from the array of targets are being disposed at different elevations relative to remaining targets from the array of targets.

A feature of this embodiment is that targets in the array of targets are provided in a plurality of colors.

A feature of this embodiment is that each target in the array of targets comprises a circuit and a light emitting member responsive to actuation of the circuit by a motion of the target or by a patient touch to emit light.

A feature of this embodiment is that each target in the array of targets comprises a circuit and a sound emitting member responsive to actuation of the circuit by a motion of the target or by a patient touch to emit sound.

In an embodiment, a method of assessing or managing a medical condition or an impairment in a patient comprises the steps of providing a device comprising an elongated base member, markings disposed on one surface of the elongated base member along a length of the elongated base member, targets disposed, during use of the device, below a bottom edge of the elongated base member, and coupling members, each coupling member couples a respective target from the targets to the elongated base member for a reciprocal linear movement along the length of the elongated base member; positioning the device adjacent a patient or positioning the patient adjacent the device; reaching, by the patient having his/her arm extended, from a starting position in a direction along the elongated base member toward one or more targets; and measuring, with the markings, a distance traveled by the arm of the patient along the length of the elongated base member.

A feature of this embodiment is that the step of reaching comprises a step of extending, by the patient, his/her arm in a direction being generally parallel with the elongated base member.

A feature of this embodiment is that method further comprises a step of fitting the patient with a harness and a step of supporting, with the harness, the patient reaching the one or more targets.

A feature of this embodiment is that method further comprises a step of fitting the patient with a harness and a step of connecting the harness to a resistance inducing and resilient member.

A method of assessing or managing a medical condition or an impairment in a patient comprises the steps of positioning targets in a two-dimensional array and at different elevations from each other and in a relationship to a shoulder height of the patient; reaching, by the patient having his/her arm extended, from a starting position toward one or more targets; and assessing at least one of a distance and an angle traveled by the arm of the patient from the starting position based on specific target(s) reached by the patient.

In an embodiment, a method of a non-surgical management of a low back impairment in a patient comprises the steps of providing a device comprising a support member, a base member mounted on the support member, and a two-dimensional array of targets suspended by coupling members from the base member, some targets from the two-dimensional array of targets are being disposed at different elevations relative to remaining targets from the two-dimensional array of targets; positioning the device in front of the patient or positioning the patient in front of the device; reaching, by the patient having his/her arm extended, in a direction of a target or targets in the array of targets; observing, by a medical practitioner, the target or targets reached or not reached by the patient; determining, by the medical practitioner, a degree of the low back impairment based on position of the target or targets reached or not reached by the patient; and prescribing, by the medical practitioner, based on the degree of the low back impairment, an exercise and/or therapy regimen promulgating improvement in the low back impairment.

A feature of this embodiment is that the step of reaching the one or more targets comprises pivoting a torso relative to a trunk.

A feature of this embodiment is that the step of reaching the one or more targets comprises reaching across an upper body.

A feature of this embodiment is that the step of reaching the one or more or targets comprises leaning forward or to one or both sides while reaching across an upper body.

A feature of this embodiment is that the method further comprises a step of audibly annunciating a condition where the patient reached the one or more targets.

A feature of this embodiment is that the method further comprises a step of visually annunciating a condition where the patient reached the one or more targets.

A feature of this embodiment is that the step of visually annunciating the condition where the patient reached the one or more targets comprises a step of providing the targets in a plurality of colors.

A feature of this embodiment is that the step of reaching the one or more or targets comprises a step of not moving feet.

A feature of this embodiment is that the step of determining the degree of the low back impairment comprises a step of determining a range of targets reached by the patient in a three-dimensional space.

In an embodiment, a functional reach assessment device, comprises an elongated base member comprising a pair of surface spaced apart from each other to define a thickness of the elongated base member; markings disposed on one surface from the pair of surfaces of the elongated base member along a length of the elongated base member; targets disposed, during use of the device, below a bottom edge of the elongated base member; and coupling members, each coupling member couples a respective target from the targets to the elongated base member for a reciprocal linear movement along the length of the elongated base member.

In an embodiment, a method of assessing or managing a medical impairment in a patient comprising the steps of providing a wearable device comprising at least a tilt sensor and a distance measurement device; attaching the wearable device to an upper body portion of a patient; moving the upper body portion through one or more preselected motions; and measuring at least one of a bend angle of the upper body portion and a distance traveled by the wearable device during a movement of the upper body portion through the one or more preselected motions, where angular and/or linear movement results characterize the medical impairment.

A feature of this embodiment is that the wearable device is a smartwatch worn on a wrist of the patient during the movement of the upper body portion.

A feature of this embodiment is that the wearable device is glasses worn on a head of the patient during the movement of the upper body portion.

A feature of this embodiment is that the method further comprises a step of displaying angular and/or linear movement results on a display in the wearable device.

A feature of this embodiment is that the method further comprises a step of communicating the angular and/or linear movement results to a remote location and a step of displaying the angular and/or linear movement results on a display in the remote location.

A feature of this embodiment is that the step of moving comprises a step of establishing a starting position with the wearable device.

In an embodiment, a method of assessing or managing a medical condition or an impairment in a patient comprises the steps of providing a hand-held distance and/or angle measuring device; holding the hand-held distance and/or angle measuring device by a hand of the patient during an assessment or a management of the medical impairment; moving the hand through one or more preselected motions; and measuring at least one of a travel angle of the hand-held distance and/or angle measuring device and a distance traveled by the hand-held distance and/or angle measuring device during a movement of the hand through the one or more preselected motions.

In an embodiment, a method of assessing or managing a medical condition or an impairment in a patient comprises the steps of providing a display; displaying a set of markings on the display; positioning a fist of an extended arm of a patient at a preselected starting position relative to the set of markings; reaching, with the extended arm from, the starting position in a direction of one or more selected markings; and measuring a distance traveled by the extended arm.

A feature of this embodiment is that the step of reaching comprises a step of bending an upper body in a relationship to a waist of the patient.

A feature of this embodiment is that the step of reaching comprises a step of reaching with the extended arm across an upper body of the patient.

The chosen exemplary embodiments have been described and illustrated, to plan and/or cross section illustrations that are schematic illustrations of idealized embodiments, for practical purposes so as to enable any person skilled in the art to which it pertains to make and use the same. As such, variations from the shapes of the illustrations as a result, for example, of manufacturing techniques and/or tolerances, are to be expected. It is therefore intended that all matters in the foregoing description and shown in the accompanying drawings be interpreted as illustrative and not in a limiting sense. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope. It will be understood that variations, modifications, equivalents and substitutions for components of the specifically described exemplary embodiments of the invention may be made by those skilled in the art without departing from the spirit and scope of the invention.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

To the extent that the appended claims have been drafted without multiple dependencies, it should be noted that all possible combinations of features which would be implied by rendering the claims multiply dependent are explicitly envisaged and should be considered part of the invention.

Anywhere the term "comprising" is used, embodiments and components "consisting essentially of" and "consisting of" are expressly disclosed and described herein.

Furthermore, the Abstract is not intended to be limiting as to the scope of the claimed subject matter and is for the purpose of quickly determining the nature of the claimed subject matter.

What is claimed is:

1. A mobility assessment device, comprising:
    an elongated base member comprising a pair of surfaces spaced apart from each other to define a thickness of said elongated base member;
    markings disposed on one surface from said pair of surfaces of said elongated base member along a length of said elongated base member;
    targets disposed, during use of said mobility assessment device, below a bottom edge of said elongated base member; and
    coupling members, each coupling member coupling a respective target from said targets to said elongated base member for a reciprocal linear movement of said respective target along said length of said elongated base member.

2. The mobility assessment device of claim 1, wherein said each coupling member comprises:
    a mounting member configured to cage a portion of said elongated base member; and
    a member that connects said respective target to said mounting member.

3. The mobility assessment device of claim 1, wherein said elongated base member comprises a pair of members and wherein said mobility assessment device comprises a hinge coupling said pair of members therebetween.

4. The mobility assessment device of claim 1, further comprising a means for supporting said elongated base member at an elevation above a surface that a patient stands or sits on during said use of said mobility assessment device.

5. The mobility assessment device of claim 4, wherein said means comprises a support member that is disposed vertically, said support member configured to support said elongated base member at an elevation above a surface that a patient stands or sits on during said use of said mobility assessment device.

6. The mobility assessment device of claim 5, wherein said support member comprises adjustable portions.

7. The mobility assessment device of claim 5, further comprising a base so that said support member is mounted in a free-standing manner, said elongated base member being stationary mounted at a free end of said support member.

8. The mobility assessment device of claim 7, wherein said base comprises a tri-pod.

9. The mobility assessment device of claim 5, wherein said support member comprises a rail, said elongated base member being mounted, in a generally horizontal direction, on said rail for a reciprocal linear movement along said rail in a vertical direction.

10. The mobility assessment device of claim 5, wherein said elongated base member is configured as a pair of half portions and wherein said means comprises a scissor mechanism that comprises portions thereof being rigidly secured to each of the pair of half portions, said pair of half portions being configured to move between an operable first position where the elongated base member is disposed generally horizontally and a folding second position where the half portions are either disposed parallel to said support member or at an incline to said support member, said pair of half portions disposable in an intermediate position anywhere between said first and second positions.

11. The mobility assessment device of claim 4, wherein said means comprises one or more apertures through said thickness of said elongated base member.

12. The mobility assessment device of claim 4, wherein said means comprises a pivot between one end of said elongated base member and a structure so that said elongated base member pivots in a generally horizontal plane.

13. A mobility assessment device, comprising:
    a support member disposed vertically during use of said mobility assessment device;
    an elongated base member comprising a pair of surfaces spaced apart from each other to define a thickness of said elongated base member, said elongated base member being mounted in a generally horizontal direction at or adjacent a top end of said support member;
    markings disposed on one surface from said pair of surfaces of said elongated base member along a length of said elongated base member;
    targets disposed, during use of said mobility assessment device, below a bottom edge of said elongated base member; and
    coupling members, each coupling member coupling a respective target from said targets to said elongated base member for a reciprocal linear movement of said respective target along said length of said elongated base member.

14. The mobility assessment device of a claim 13, wherein said elongated base member comprises a notch, said notch running along a length of said elongated base member and defining a reduced thickness portion of said elongated base member at a top edge thereof, and wherein said each coupling member comprises:
    a J-shaped mounting member configured to partially cage or partially envelope said reduced thickness portion, said J-shaped mounting member comprising a flange being disposed in said notch during said use of said mobility assessment device; and
    a member coupling said respective target to a free end of said J-shaped mounting member, said free end configured to extend past said bottom edge of said elongated base member.

15. A mobility assessment device, comprising:
    a base member;
    a support member that couples to said base member and that supports said base member above a surface that a patient stands or sits on during use of said mobility assessment device;
    an array of targets suspended from said base member, some a targets from said array of targets being disposed at different elevations relative to remaining targets from said array of targets; and
    coupling members, each coupling member coupling a respective target from said array of targets to said base member for a reciprocal linear movement of said respective target along a length of said base member.

16. The mobility assessment device of claim 15, wherein targets in said array of targets are provided in a plurality of colors.

17. The mobility assessment device of claim 15, wherein each target in said array of targets comprises a circuit and a light emitting member responsive to actuation of said circuit by a motion of said each target or by a patient touch to emit light.

18. The mobility assessment device of claim 15, wherein each target in said array of targets comprises a circuit and a sound emitting member responsive to actuation of said circuit by a motion of said each target or by a patient touch to emit sound.

19. A mobility assessment system, comprising:
- an elongated base member comprising a pair of surfaces spaced apart from each other to define a thickness of said elongated base member;
- markings disposed on one surface from said pair of surfaces of said elongated base member along a length of said elongated base member;
- targets disposed, during use of said mobility assessment system, below a bottom edge of said elongated base member;
- coupling members, each coupling member coupling a respective target from said targets to said elongated base member for a reciprocal linear movement of said respective target along said length of said elongated base member; and
- a harness configured to be worn by a patient undergoing a mobility assessment, said harness configured to be held by a medical practitioner during said mobility assessment.

20. The mobility assessment system of claim 19, further comprising:
- a resistance inducing member being one of a spring and an exercise band; and
- a connection between said harness and said resistance inducing member.

21. A mobility assessment device, comprising:
- an elongated base member, comprising:
  - a pair of surfaces spaced apart from each other to define a thickness of said elongated base member, and
  - a notch, said notch running along a length of said elongated base member, said notch defining a reduced thickness portion of said elongated base member at a top edge thereof;
- markings disposed on one surface from said pair of surfaces of said elongated base member along a length of said elongated base member;
- targets disposed, during use of said mobility assessment device, below a bottom edge of said elongated base member; and
- coupling members, each coupling member comprising:
  - a J-shaped mounting member configured to partially cage or partially envelope said reduced thickness portion, said J-shaped mounting member comprising a flange being disposed in said notch during said use of said mobility assessment device, and
  - a member coupling a respective target from said targets to a free end of said J-shaped mounting member, said free end configured to extend past said bottom edge of said elongated base member;
- said each coupling member coupling said respective target to said elongated base member for a reciprocal linear movement of said respective target along said length of said elongated base member.

* * * * *